(12) United States Patent
    Shinoda

(10) Patent No.: US 12,692,521 B2
(45) Date of Patent: Jul. 28, 2026

(54) METHOD FOR PRODUCING FAT/OIL

(71) Applicant: Amano Enzyme Inc., Nagoya (JP)

(72) Inventor: Tatsuya Shinoda, Kakamigahara (JP)

(73) Assignee: Amano Enzyme Inc., Nagoya (JP)

( * ) Notice: Subject to any disclaimer, the term of this patent is extended or adjusted under 35 U.S.C. 154(b) by 606 days.

(21) Appl. No.: 17/905,859

(22) PCT Filed: Mar. 10, 2021

(86) PCT No.: PCT/JP2021/009480
    § 371 (c)(1),
    (2) Date: Sep. 8, 2022

(87) PCT Pub. No.: WO2021/182501
    PCT Pub. Date: Sep. 16, 2021

(65) Prior Publication Data
    US 2023/0133917 A1     May 4, 2023

(30) Foreign Application Priority Data

Mar. 11, 2020     (JP) ................................ 2020-042390

(51) Int. Cl.
    *C12P 7/64*       (2022.01)
    *C12N 9/20*       (2006.01)
    *C12N 11/00*      (2006.01)
(52) U.S. Cl.
    CPC .................. *C12P 7/64* (2013.01); *C12N 9/20* (2013.01); *C12N 11/00* (2013.01); *C12Y 301/01003* (2013.01)
(58) Field of Classification Search
    CPC ....... C12P 7/64–6472; C12N 11/00–14; C12N 9/20; C12Y 301/01003
    See application file for complete search history.

(56) References Cited

U.S. PATENT DOCUMENTS 5,128,251 A  *  7/1992  Yokomichi ........... C12P 7/6454
                                                                      435/177
2018/0030485 A1    2/2018  Watanabe

FOREIGN PATENT DOCUMENTS

| | | |
|---|---|---|
| EP | 0305901 B1 | 4/1995 |
| JP | 63-240790 A | 10/1988 |
| JP | 64-002588 A | 1/1989 |
| JP | 01-225490 A | 9/1989 |
| JP | H01-120295 A | 12/1989 |
| JP | 02-174676 A | 7/1990 |
| MY | 103219 A | 5/1993 |
| WO | WO 2012/077614 A1 | 6/2012 |
| WO | WO 2016/133004 A1 | 8/2016 |
| WO | WO 2019/155789 A1 | 8/2019 |

OTHER PUBLICATIONS

Product Specificaiton for Lipase PS Amano IM, Dec. 1, 2017, 1 page. Document provided with response on Jun. 12, 2025 (Year: 2017).*
Product Specificaiton for Lipase DF Amano IM, Mar. 1, 2023, 2 pages. Document provided with response on Jun. 12, 2025 (Year: 2023).*
Kimura et al. "Enzymatic editing of vegetable oils to obtain a low diglyceride (DG) oil by two methods" 1 page. AOCS 2021 Document provided with response on Jun. 12, 2025 (Year: 2021).*
Extended European Search Report issued for counterpart European Patent Application No. 21767443.1, issued on Nov. 20, 2023.
International Search Report in PCT/JP2021/009480, issued May 11, 2021.

* cited by examiner

*Primary Examiner* — Thane Underdahl
(74) *Attorney, Agent, or Firm* — Knobbe, Martens, Olson & Bear, LLP

(57)     ABSTRACT
The present invention addresses the problem of providing an effective new means for efficiently reducing the amount of diacylglycerol in a fat/oil (by conversion into triacylglycerol). Disclosed is a method for producing a fat/oil, including a step in which a lipase having a ratio of transesterification activity to hydrolysis activity of 0.007 or higher is caused to act on a diacylglycerol-containing fat/oil.

5 Claims, No Drawings

1

METHOD FOR PRODUCING FAT/OIL

TECHNICAL FIELD

The present invention relates to a method for producing a fat/oil. Specifically, the present invention relates to a method for producing a fat/oil using a lipase.

BACKGROUND ART

Fats/oils such as palm oil are converted into high quality fats/oils by removal of diacylglycerol or conversion into triacylglycerol (see, for example, Patent Document 1). Fats/oils having high added value have been produced by modifying the fatty acid composition of triacylglycerol using a transesterification reaction of a lipase (see, for example, Patent Documents 2 and 3). In general, two steps are required when both removal of diacylglycerol/conversion into triacylglycerol and modification of the fatty acid composition of triacylglycerol are performed.

Patent Document 1 above discloses reducing the amount of diacylglycerol of a diacylglycerol-containing fat/oil and changing the fatty acid composition of triacylglycerol by using a lipase derived from the genus of *Pseudomonas* or the genus of *Rhizopus*. Patent Document 1 shows that the yield of triacylglycerol decreases when the moisture content of a fat/oil on which an enzyme acts is 110 ppm or more.

On the other hand, Patent Document 4 discloses a lipase derived from *Penicillium* sp. as a lipase that can be used for production and modification of a fat/oil. It is said that the lipase acts on monoglyceride (monoacylglycerol) and diglyceride (diacylglycerol), but does not act on triglyceride (triacylglycerol) at all.

PRIOR ART DOCUMENTS

Patent Documents

Patent Document 1: Japanese Patent Laid-open Publication No. S64-2588
Patent Document 2: WO 2012/077614 A
Patent Document 3: WO 2019/155789 A
Patent Document 4: Japanese Patent Laid-open Publication No. H2-174676

SUMMARY OF THE INVENTION

Problems to be Solved by the Invention

Under the above background, an object of the present invention is to provide an effective new means for efficiently reducing diacylglycerol in a fat/oil (by conversion into triacylglycerol).

Means for Solving the Problem

In order to solve the above problems, studies have been repeated focusing on the "ratio of hydrolysis activity and transesterification activity" of an enzyme to be used, and as a result, a method for efficiently and effectively modifying a fat/oil (in other words, a method for producing a modified fat/oil) has been found. The following inventions are provided based on the results.

[1] A method for producing a fat/oil, including a step in which a lipase having a ratio of transesterification activity to hydrolysis activity of 0.007 or more is caused to act on a diacylglycerol-containing fat/oil.

2

[2] The method for producing a fat/oil described in [1], in which a moisture content of the diacylglycerol-containing fat/oil is 110 ppm or more.

[3] The production method described in [1] or [2], in which the ratio is 0.01 or more.

[4] The production method described in any one of [1] to [3], in which the lipase is an immobilized lipase.

[5] The production method described in any one of [2] to [4], in which the moisture content is 1000 ppm or less.

[6] A method for producing a fat/oil, including a step in which a lipase having a ratio of transesterification activity to hydrolysis activity of 0.001 or more is caused to act on a diacylglycerol-containing fat/oil having a moisture content of less than 110 ppm.

EMBODIMENTS OF THE INVENTION

The present invention relates to a method for producing a fat/oil using a lipase. The production method of the present invention is characterized by a step in which a lipase having a ratio of transesterification activity to hydrolysis activity, that is, "transesterification activity/hydrolysis activity" of 0.007 or more is caused to act on a diacylglycerol-containing fat/oil, preferably a step in which a lipase having a ratio of "transesterification activity/hydrolysis activity" of 0.007 or more is caused to act on a diacylglycerol-containing fat/oil having a moisture content of 110 ppm or more, or a step in which a lipase having the ratio of 0.001 or more is caused to act on a diacylglycerol-containing fat/oil having a moisture content of less than 110 ppm. In the step, diacylglycerol in the diacylglycerol-containing fat/oil reacts with free fatty acid or free fatty acid ester by the action of the lipase to produce triacylglycerol. As a result, the fat/oil is modified. In other words, a modified fat/oil is obtained.

The lipase usually exhibits hydrolysis activity in the case of a water-based reaction system and usually exhibits transesterification activity in the case of an oil-based reaction system. The lipase is subjected to a treatment such as immobilization to improve the transesterification activity. Conventionally, in the case of performing a transesterification reaction or an ester synthesis reaction in an oil-based reaction system, it has been common to determine an enzyme using only transesterification activity as an index. However, since the substrate (such as a fat/oil) contains moisture even in a trace amount, it is considered that the hydrolysis activity may also affect the reaction efficiency and the like. As a result of studies based on this idea, it has been found that the ratio of hydrolysis activity and transesterification activity is important for the efficiency of the ester synthesis reaction in an oil-based reaction system, and the present invention has been completed. The ratio of hydrolysis activity and transesterification activity can be calculated as follows. The hydrolysis activity and the transesterification activity can be measured by methods described below.

Regarding the hydrolysis activity, first, the hydrolysis activity of the lipase before an immobilization treatment is measured. Then, a hydrolysis activity value per 1 g of the immobilized lipase is calculated from the amount of the lipase used in the immobilization treatment. For example, when the hydrolysis activity of the lipase before the immobilization treatment is 10000 u/g and 1 g (equivalent to 1 g in terms of activity) of this lipase is used for immobilization, and as a result, 4 g of the immobilized lipase is obtained, the hydrolysis activity value used for calculating the ratio to the transesterification activity is 10000 u/g×1 g÷4 g=2500 u/g. On the other hand, for the transesterification activity, a lipase after the immobilization treatment is used. That is, the transesterification activity of the immobilized lipase is measured by the method described below, and the measurement result (transesterification activity value of the immobilized lipase) is used for calculating the ratio to the hydrolysis activity. The above is the calculation method in the case of the immobilized lipase, but lipases treated by methods other than immobilization can also be calculated for each activity in the same manner. In the case of an untreated lipase, the measured values (hydrolysis activity value and transesterification activity value) may be directly used for calculating the ratio.

The ratio of transesterification activity to hydrolysis activity of the lipase is not particularly limited as long as the diacylglycerol in the diacylglycerol-containing fat/oil can be reduced by the ester synthesis reaction. An example of the above ratio is preferably 0.007 or more when the lipase is caused to act on a diacylglycerol-containing fat/oil having a moisture content of 110 ppm or more. From the viewpoint of further reducing diacylglycerol in the diacylglycerol-containing fat/oil, the ratio in this example is preferably 0.01 or more, more preferably 0.02 or more, even more preferably 0.03 or more, further preferably 0.05 or more, and still more preferably 0.07 or more. The upper limit of the ratio is not particularly limited, and is, for example, 0.5 or less, 0.3 or less, or 0.1 or less.

Another example of the above ratio is preferably 0.001 or more when the lipase is caused to act on a diacylglycerol-containing fat/oil having a moisture content of less than 110 ppm. From the viewpoint of further reducing diacylglycerol in the diacylglycerol-containing fat/oil, the ratio in this example is preferably 0.002 or more and more preferably 0.003 or more. The upper limit of the ratio is not particularly limited, and is, for example, 0.5 or less, 0.3 or less, 0.1 or less, 0.05 or less, 0.01 or less, or 0.005 or less.

The origin of the lipase is not particularly limited as long as the ratio of transesterification activity to hydrolysis activity satisfies the above conditions. For example, a lipase derived from the genus of *Rhizopus, Penicillium, Burkholderia, Aspergillus, Candida, Pseudomonas, Mucor, Thermomyces,* or *Geotrichum* can be used. Preferably, a lipase derived from the genus of *Rhizopus, Penicillium,* or *Burkholderia* is employed. An example of the lipase derived from the genus of *Rhizopus* is a lipase produced by *Rhizopus oryzae* (a specific example is Lipase DF (Amano Enzyme Inc.)), an example of the lipase derived from the genus of *Penicillium* is a lipase produced by *Penicillium camenberti* (a specific example is Lipase G (Amano Enzyme Inc.)), and an example of the lipase derived from the genus of *Burkholderia* is a lipase produced by *Burkholderia cepacia* (a specific example is Lipase PS (Amano Enzyme Inc.)).

One kind of the lipases described above may be used alone, or a plurality of kinds thereof may be used in combination. When the lipase is caused to act on a diacylglycerol-containing fat/oil having a moisture content of 110 ppm or more, among the lipases described above, a lipase derived from the genus of *Rhizopus* (preferably *Rhizopus oryzae*) or the genus of *Penicillium* (preferably *Penicillium camenberti*) is preferably mentioned, and a lipase derived from the genus of *Rhizopus* (preferably *Rhizopus oryzae*) is more preferably mentioned.

When the lipase is caused to act on a diacylglycerol-containing fat/oil having a moisture content of less than 110 ppm, among the lipases described above, a lipase derived from the genus of *Rhizopus* (preferably *Rhizopus oryzae*) or the genus of *Burkholderia* (preferably *Burkholderia cepa-*

*cia*) is preferably mentioned, and a lipase derived from the genus of *Burkholderia* (preferably *Burkholderia cepacia*) is more preferably mentioned.

In an embodiment of the present invention, a lipase immobilized on a carrier (immobilized lipase) is used. The immobilized lipase can be prepared by a conventional method. A commercially available immobilized lipase can also be used. A treatment such as immobilization can also be used to change the ratio of transesterification activity to hydrolysis activity.

Examples of the fat/oil on which the lipase acts may include vegetable fats/oils such as soybean oil, rapeseed oil, rice oil, corn oil, sunflower oil, cottonseed oil, peanut oil, safflower oil, olive oil, palm oil, palm soft oil, palm fractionated oil, palm kernel oil, coconut oil, and cocoa butter, animal fats/oils such as fish oil, lard, beef tallow, and milk fat, fractionated oils or hardened oils of these, and synthetic fats/oils such as trilaurin, triolein, and tripalmitin.

If necessary, fatty acids such as myristic acid, palmitic acid, stearic acid, oleic acid, linoleic acid, linolenic acid, and γ-linolenic acid, or esters thereof (hereinafter, "fatty acid and the like" is used as a comprehensive expression of fatty acid and fatty acid ester) may be added to the fat/oil alone or in combination of two or more kinds thereof. These fatty acids may be originally contained in the fat/oil. The addition amount or content of the fatty acid and the like is, for example, 1 to 1000 parts by weight, preferably 1.5 to 100 parts by weight, more preferably 2 to 30 parts by weight, and further preferably 2.5 to 10 parts by weight, 3 to 7.5 parts by weight, or 3.5 to 5 parts by weight, per 100 parts by weight of the fat/oil.

In order to perform an ester synthesis reaction using a lipase, for example, a lipase may be added to a diacylglycerol-containing fat/oil and reacted. Specifically, the moisture content (moisture concentration; hereinafter, simply described as "moisture content") of the reaction system (including a stock oil (fat/oil, or a mixture of a fat/oil and a fatty acid, etc.) and an enzyme) at the time of start of the reaction is not particularly limited, and the reaction is performed by adjusting the moisture content to less than 110 ppm (for example, 10 ppm or more and less than 110 ppm, preferably 40 to 105 ppm, more preferably 60 to 100 ppm, and further preferably 80 to 97 ppm) or 110 ppm or more (for example, 110 to 1000 ppm, preferably 150 to 800 ppm, more preferably 200 ppm to 500 ppm, further particularly 200 ppm to 400 ppm, and even more preferably 220 to 300 ppm), and then adding the lipase. As the moisture content of the reaction system increases, a hydrolysis reaction is more likely to occur than the ester synthesis reaction. Therefore, when the moisture content of the reaction system is large, the ratio of transesterification activity to hydrolysis activity of the lipase is preferably high.

For example, the reaction is performed for a predetermined time (for example, 1 hour to 48 hours) under the condition of 30 to 100° C., preferably 35 to 80° C. In order to accelerate the reaction, stirring may be performed during the reaction. In addition to a batch-type reaction, a continuous reaction using a column, a fluidized tank, or the like can be adopted. For a reaction using an immobilized lipase, a batch-type stirring vessel reactor, a flow-type stirring vessel reactor, a packed bed-type reactor, a fluidized bed-type reactor, or the like can be used.

The addition amount of the lipase is not particularly limited as long as a desired reaction proceeds. For example, 10 to 100 parts by weight of the lipase may be added per 100 parts by weight of the stock oil.

When the ester synthesis reaction proceeds, moisture is generated along with the generation of triacylglycerol, and thus it is preferable to remove the moisture from the reaction system. For example, the moisture can be removed by distillation under reduced pressure, use of a dehydrating agent such as a molecular sieve, and use of a dry inert gas such as nitrogen gas.

EXAMPLES

The diacylglycerol (DG) reducing effect (Test Examples 1 and 2) of various lipases having different ratios of transesterification activity to hydrolysis activity was examined. The hydrolysis activity and the transesterification activity were measured by the following methods.
(Hydrolysis Activity Measuring Method)

The hydrolysis activity was measured using Lipase Kit S (SB Bioscience Co., Ltd.). A coloring stock solution was prepared by adding 2.4 mL of a pH 7.0-adjusted buffer solution attached to the kit and 22 mL of purified water to the coloring agent attached to the kit. To 250 µL of the coloring stock solution, 250 µL of a pH 7.0-adjusted buffer solution attached to the kit and 2000 µL of purified water were added to obtain a coloring liquid. In a test tube, 1 mL of the coloring liquid and 50 µL of a diluent prepared by diluting an enzyme solution to an appropriate concentration were placed, and kept at 37° C. for 5 minutes. Then, 100 µL of the substrate solution attached to the kit was added, the mixture was further reacted at 37° C. for 15 minutes, and then 2 mL of acetone was added to stop the reaction. The supernatant of the sample after the reaction was stopped was recovered, and the absorbance was measured at 412 nm. The substrate solution added after the addition of acetone was used as a blank, and the hydrolysis activity (U/g) was calculated from the following calculation formula.

$$\text{Hydrolysis activity (U/g)}=(A412\text{ sample}-A412\text{ blank})\times 20 \times n$$

wherein A412 sample is the absorbance of the supernatant of the sample at 412 nm, A412 blank is the absorbance of the blank at 412 nm, 20 is a coefficient, and n is a dilution factor of the enzyme solution.
(Transesterification Activity Measuring Method)

To a 50-mL disposable centrifuge tube, 5 mL of tricaprylin (manufactured by Wako Pure Chemical Industries, Ltd.) and 6 mL of methyl laurate (manufactured by Wako Pure Chemical Industries, Ltd. are added, and preheated at 30±1° C. for 10 minutes. After 0.1 g of an enzyme sample was added, the tube was covered with a lid, and mixing by inversion was performed, the tube was set in a rotator, and an enzyme reaction at 30° C. and 50 rpm for 30 minutes. A gas chromatography sample was prepared by dissolving 30 µL of the solution after the reaction in 1 mL of hexane.

The area value of methyl caprylate generated as a result of the enzyme reaction (transesterification) was determined by gas chromatography analysis (column: DB-1HT (Agilent J&W, 5 m×0.25 mm, df 0.1 µm), temperature conditions: 50° C., held for 1 minute, then heated to 370° C. at a rate of 40° C./min, detector: FID, carrier gas: helium), and the transesterification activity was calculated by following formula.

$$\text{Transesterification activity}(u/g)=A/a-34\times\tfrac{1}{30}\times 1/0.1\times 11$$

A: Area value of methyl caprylate of sample
a: Slope calculated from calibration curve (area value of methyl octanoate=a×methyl octanoate concentration) created from area value and methyl octanoate concentration (mmol/L) when 1 mmol/L to 7.5 mmol/L of methyl octanoate is subjected to gas chromatography under the above conditions
34: Dilution factor when reaction liquid is diluted in hexane*(1 mL+30 µL)/30 µL □34
$\frac{1}{30}$: Conversion coefficient per minute of reaction time
1/0.1: Conversion coefficient per 1 g of sample
11: Amount of reaction liquid (mL)·X·5 mL of tricaprylin+6 mL of methyl laurate

Test Example 1

1. Method
(1) Preparation of Enzyme Sample

Respective lipases (*Rhizopus oryzae*-derived lipase and *Burkholderia cepacia*-derived lipase) were prepared according to a conventional method, and the hydrolysis activity and the transesterification activity were measured. The hydrolysis activity and the transesterification activity of each lipase are shown in Table 1.
(2) Preparation of Substrate Fat/Oil A fat/oil obtained by mixing glycerol dioleate, palmitic acid, and oleic acid with purified palm oil (TG content: 89.4 wt %. DG content: 6.7 wt %, residue mainly composed of fatty acids) was dried under reduced pressure at 80° C. for 12 hours or longer until the water content therein reached 95 ppm.
(3) Reaction To an Erlenmeyer flask, 0.2 g of the enzyme sample, 10 g of molecular sieve 3 A dried under reduced pressure at 180° C. for 12 hours or longer, and 20 g of substrate fat/oil were added and shaken at 60° C. and 160 rpm to cause a reaction. The reaction liquid after 22 hours was subjected to GC analysis to check a change in composition of the substrate fat/oil. The DG residual ratio was calculated from the DG ratio before and after the reaction.
2. Result The DG reducing effect of each sample (the moisture content of the reaction system at the time of start of the reaction: 95 ppm) is shown in the following table.

TABLE 1

| | Lipase | Hydrolysis activity | Transesterification activity | Activity ratio (transesterification activity/ hydrolysis activity) | DG residual ratio |
|---|---|---|---|---|---|
| Sample 1 | *Rhizopus oryzae*-derived lipase | 56000 | 60 | 0.001 | 44% |
| Sample 2 | *Burkholderia cepacia*-derived lipase | 240000 | 700 | 0.003 | 32% |

When the moisture content was 95 ppm, the DG reducing effect could be confirmed even when a lipase having a low ratio of hydrolysis activity and transesterification activity was used.

Test Example 2

1. Method (1) Enzyme Sample

A commercially available immobilized enzyme (LDF-IM, LGS-IM, and LPS-IM, all manufactured by Amano Enzyme Inc.) was used as an enzyme sample. In the above enzyme names, "L" stands for Lipase, "DF," "GS," and "PS" stand ratio of hydrolysis activity and transesterification activity (LPS-IM), but the DG reducing effect could be confirmed in other lipases having a high ratio of hydrolysis activity and transesterification activity. It was suggested that the ratio of hydrolysis activity and transesterification activity is more important than the activity amount for the DG reducing effect.

The fatty acid composition of each sample after the reaction is shown in the following table.

TABLE 3

| | Fatty acid composition ratio | | | | | | | |
| | PPP | | PPO | | POO | | OOO | |
| | Composition ratio | Ratio compared to theoretical value | Composition ratio | Ratio compared to theoretical value | Composition ratio | Ratio compared to theoretical value | Composition ratio | Ratio compared to theoretical value |
|---|---|---|---|---|---|---|---|---|
| None (substrate) | 6.8% | | 36.0% | | 37.8% | | 10.4% | |
| Theoretical value | 7.2% | 100% | 36 6% | 100% | 39.7% | 100% | 11.7% | 100% |
| Sample 3  LDP-IM | 9.3% | 129% | 34.1% | 93% | 39.2% | 99% | 13.9% | 119% |
| Sample 4  LGS-IM | 7.4% | 102% | 36.2% | 99% | 39.9% | 100% | 12.0% | 102% |
| Sample 5  LPS-IM | 10.3% | 143% | 31.6% | 87% | 36.2% | 91% | 14.0% | 119% | for the origin of the lipase, and "IM" stands for IMmobilization. Immobilized lipase DF is sold under the trade name "LDF-IM". immobilized lipase PS is sold under the trade name "LPS-IM", and immobilized Lipase GS is identified by the label "LGS-IM".

(2) Preparation of Substrate Fat/Oil

Crude palm oil (hereinafter, CPO) (TG content: 92.5 wt %, DG content: 4.8 wt %, residue mainly composed of fatty acids) was dried under reduced pressure at 80° C. for 2 hours or longer to adjust the water content to 228 ppm.

(3) Reaction

To an Erlenmeyer flask, 1 g of the enzyme sample, 10 g of molecular sieve 3 A dried under reduced pressure at 180° C. for 12 hours or longer, and 20 g of substrate fat/oil were added and shaken at 60° C. and 160 rpm to cause a reaction. The reaction liquid after 24 hours was subjected to GC analysis to check a change in composition of the substrate fat/oil.

2. Result

The DG reducing effect of each sample (the moisture content of the reaction system at the time of start of the reaction: 228 ppm) is shown in the following table.

TABLE 2

| | Lipase | Hydrolysis activity | Transester- ification activity | Activity ratio (transester- ification activity/ hydrolysis activity) | DG residual ratio |
|---|---|---|---|---|---|
| Sample 3 | LDF - IM | 8200 | 700 | 0.085 | 14% |
| Sample 4 | LGS - IM | 2200 | 65 | 0.030 | 36% |
| Sample 5 | LPS - IM | 19000 | 110 | 0.006 | 84% |

When the moisture content was 228 ppm, the DG reducing effect could not be confirmed in the lipase having a low The "theoretical value" is a value obtained by calculating the composition ratio when the transesterification reaction does not occur and only the synthesis reaction of free fatty acid and DG in the substrate fat/oil occurs based on the abundance ratio of the free fatty acid and DG in the substrate fat/oil.

In Sample 3, it could be confirmed that the transesterification reaction occurred together with the ester synthesis reaction (Table 2 and Table 3). On the other hand, in Sample 4, it could be confirmed that the ester synthesis reaction occurred (Table 2), but the transesterification reaction did not occur (Table 3). In Sample 5, it could be confirmed that the ester synthesis reaction did not occur (Table 2), but the transesterification reaction occurred (Table 3). From these results, it was found that the ester synthesis reaction occurs when the ratio of hydrolysis activity and transesterification activity is high regardless of the presence or absence of the transesterification reaction ability.

INDUSTRIAL APPLICABILITY

The present invention is useful for modifying and improving physical properties of a fat/oil or fat/oil processed products (for example, shortening and margarine). For example, the present invention can be applied for the purpose of improving spreadability, improving emulsion stability, optimizing a solid fat content (SFC), improving solidifiability, selectively concentrating a specific fatty acid, producing a low trans-fatty acid content fat/oil or a low trans-fatty acid content fat/oil processed product, and the like. A fat/oil obtained by applying the present invention or a fat/oil processed product containing the same is recognized to have improved physical properties, and has high industrial utility value.

This invention is not limited at all by the description of the above-described embodiments for carrying out the invention and Examples. Various modifications are also encompassed in this invention within the scope that does not deviate from the descriptions in the claims and can be easily conceived by persons skilled in the art. The whole contents of the articles, patent publications, patents, and the like which are clearly indicated in the present specification are incorporated herein by reference.

The invention claimed is:

1. A method of converting diacylglycerol in a fat/oil into triacylglycerol, comprising:

(a) determining a moisture content of the fat/oil to be 110 ppm or more, and (b) transesterifying the diacylglycerol in the fat/oil with an immobilized lipase having a ratio of transesterification activity to hydrolysis activity of 0020 or more.

2. The method according to claim 1, wherein a moisture content of the diacylglycerol-containing fat/oil is 110 ppm or more.

3. The method according to claim 1, wherein the ratio is 0.020 or more.

4. The method according to claim 2, wherein the moisture content is 1000 ppm or less.

5. A method of converting diacylglycerol in a fat/oil into triacylglycerol, comprising:

(a) determining a moisture content of the fat/oil to be less than 110 ppm, and (b) transesterifying the diacylglycerol in the fat/oil with an immobilized lipase having a ratio of transesterification activity to hydrolysis activity of 0.001 or more.

\*   \*   \*   \*   \*